United States Patent [19]

Haynes et al.

[11] Patent Number: 4,886,505

[45] Date of Patent: Dec. 12, 1989

[54] ANTIMICROBIAL SURFACES AND INHIBITION OF MICROORGANISM GROWTH THEREBY

[75] Inventors: John L. Haynes, Chapel Hill; James D. Mansour, Raleigh, both of N.C.

[73] Assignee: Becton, Dickinson and Company, Franlin Lakes, N.J.

[21] Appl. No.: 742,662

[22] Filed: Jun. 7, 1985

[51] Int. Cl.$^4$ ............................................. A61M 25/00
[52] U.S. Cl. .................................... 604/265; 128/284; 128/788
[58] Field of Search ................ 604/265, 280; 128/389, 128/391, 788

[56] References Cited

U.S. PATENT DOCUMENTS

| | | | |
|---|---|---|---|
| 742,802 | 10/1903 | Roberts | 128/389 X |
| 1,042,124 | 10/1912 | Wagoner | 128/391 |
| 4,054,139 | 10/1977 | Crossley | . |
| 4,253,463 | 3/1981 | Kim | . |
| 4,308,859 | 1/1982 | Child | 128/788 X |
| 4,411,648 | 10/1983 | Davis et al. | . |
| 4,476,590 | 10/1984 | Scales et al. | 3/1.91 |
| 4,483,688 | 11/1984 | Akiyama | . |

FOREIGN PATENT DOCUMENTS 1582016 12/1980 United Kingdom .
8102667 10/1981 World Int. Prop. O. .

OTHER PUBLICATIONS

Marino et al., *J. Electrochem. Soc.* 132, 1985, pp. 68–71.
Thompson et al., *J. Amer. Med. Assoc.* 251, 1984, pp. 747–751.
Romans, "Oligodynamic Metals" (Chapter 24) and "Silver Compounds" (Chapter 28), *Disinfection, Sterilization and Preservation*, 1968.
Spadaro et al., *Antimicrobial Agents and Chemotherapy* 6, 1974, pp. 637–642.
Akiyama et al., *J. Urology* 121, 1979, pp. 40–42.
Davis et al., *J. Clin. Microbiology* 15, 1982, pp. 891–894.

*Primary Examiner*—Stephen C. Pellegrino
*Attorney, Agent, or Firm*—Richard E. Brown

[57] ABSTRACT

Apparatus having an antimicrobial surface includes a medical device and a plurality of metals, at least one of which is in contact with a surface of the device and in contact with a different metal. The invention includes a method to use the apparatus to treat a living body wherein the antimicrobial surface of the apparatus is contacted with a body electrolyte thereby inhibiting growth of microorganisms in the body consequent to the use of the apparatus.

1 Claim, 5 Drawing Sheets

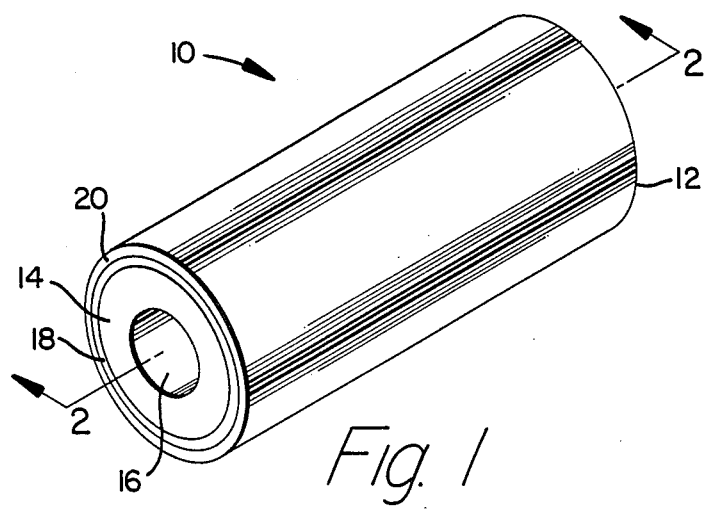
Fig. 1
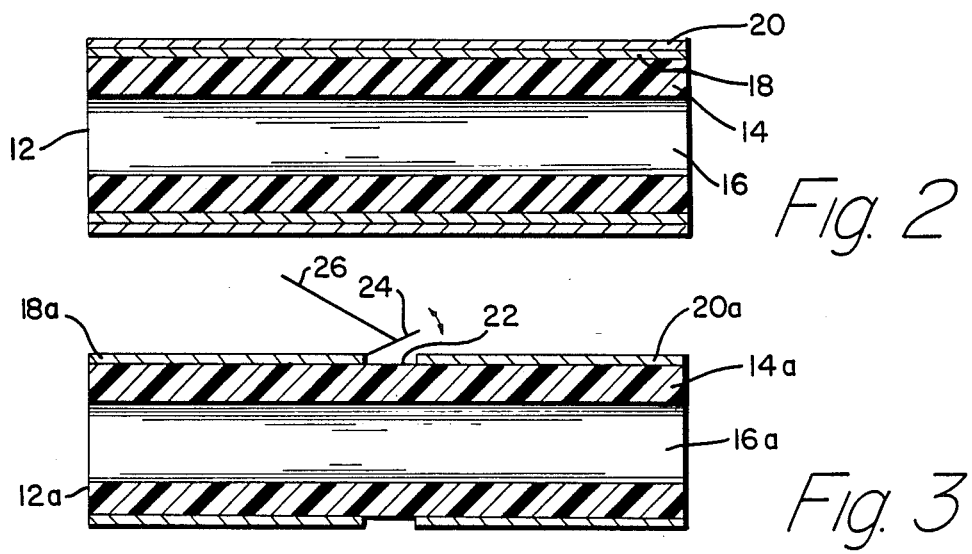
Fig. 2
Fig. 3

ANTIMICROBIAL SURFACES AND INHIBITION OF MICROORGANISM GROWTH THEREBY

BACKGROUND OF THE INVENTION

1. Field of the Invention

This invention relates to biological activity, and more particularly, it relates to medical devices having improved antimicrobial surfaces and to a method to inhibit microorganism growth in a living body during their use.

2. Description of the Prior Art

Infection is a frequent complication of indwelling medical devices such as vascular, and, in particular, urinary catheters. A high percentage of patients who require long-term urinary catheters develop chronic urinary tract infections, frequently in conjunction with episodes of fever, chills, and flank pain. Such patients are at risk of developing bacteremia or chronic pyelonephritis, conditions of high morbidity and mortality.

The magnitude of the urinary tract infection (UTI) problem is clearly indicated by statistics showing that 10–15% of hospital patients need urinary catheters and about 25% of those develop infection. Put another way, UTI accounts for 40% of all nosocomial infections and involves an estimated 800,000 patients a year.

Many studies have demonstrated that bacterial contamination of the urinary drainage bag during catheterization is a frequent source of bladder bacteriuria, and that addition of various antibacterial and antifungal agents, such as hydrogen peroxide, reduce or delay the incidence of bacteriuria. Coatings of antibacterial agents on catheters have likewise been known to delay development of bacteriuria. Thompson et al. (*J. Am. Med. Assoc.* 251 747–51 (1984)), however, showed that infections arising intraluminally from drainage bag contamination are uncommon among catheterized patients and that periodic instillation of disinfectants into closed, sterile drainage systems is not effective in reducing the incidence of catheter-associated bacteriuria. Their data suggest that extraluminal migration in the periurethral mucous sheath is the major route of bacterial entry into the catheterized urinary tract.

Another important part of medical care is infusion of drugs and fluid with intravenous catheters. Contamination of the infusion system is common and may result in septicemia. It has been suggested that microorganisms may gain access to the tip of a cannula both at the moment of insertion and subsequently by migration along the interface between the catheter and tissue.

U.S. Pat. No. 4,253,463 to Kim teaches a method of reducing infection during use of an intravascular device. The method includes applying to the device a coating of a common metal, such as aluminum or tin, which contacts the tissue of the patient at the point of entry of the device.

Silver compounds have long been used in clinical medicine because of their antiseptic properties. Two examples of such use of silver compounds are the prophylaxis of ocular infections and prevention and treatment of burn-wound sepsis. Beginning in the late 19th century, metallic silver in the form of sutures and foils was used to produce bacteriostatic effects via the passive dissociation of silver from the metallic phase into tissue. A review of this work with silver alone or in combination with other metals is given by Romans, "Oligodynamic Metals" (Chapter 24) and "Silver Compounds" (Chapter 28), *Disinfection, Sterilization and Preservation*, C. A. Lawrence and S. S. Bloek, ed., Lea and Fibiger, 1968.

Inhibition of the growth of bacteria and fungi by ions of stainless steel, silver, gold and platinum generated at electrodes had been reported by Spadaro et al. (*Antimicrobial Agents and Chemotherapy* 6, 637 (1974).

Marino et al. (*J. Electrochem. Soc.* 132, 68 (1985)) disclose wound dressings consisting of fabrics which are rendered antiseptic by coating with metallic silver and application of externally generated current through tabs serving as electrodes.

U.S. Pat. No. 4,054,139 to Crossley teaches reduction of catheter-associated infection by oligodynamic amounts of silver, or silver mixed with another heavy metal, such as gold, on both the interior and exterior surfaces of the catheter.

Akiyama et al. (*J. Urology* 121, 40 (1979)) discloses a modified urinary catheter and drainage system which includes a Foley catheter coated with silver powder and a silver plated connector between the flared end of the catheter and the synthetic drainage tube. The system utilizes the bacteriostatic property of silver ions to reduce urinary tract infection due to prolonged bladder catheterization. In U.S. Pat. No. 4,483,688 and British Pat. No. 1,582,016, Akiyama discloses use of an oligodynamically active heavy metal, such as copper, silver or gold or alloys thereof to achieve a bacteriostatic effect on the outside surface only of a catheter or urinary drainage system.

Travenol Laboratories, Inc., Medical Products Division, Deerfield, Ill., presently markets a silver coated catheter adapter designed to kill bacteria at the catheter-tubing junction.

Davis et al. in (J. Clin. Microbiology 15, 891 (1982)) describe iontophoretic killing of several bacterial genera by various metals. Only gold iontophoresis killed all bacterial genera. Other metals, such as silver and copper were described as being ineffective. In U.S. Pat. No. 4,411,648, Davis et al. teach a urinary catheter having heavy metal-containing electrodes. Bacterial infection associated with catheterization is iontophoretically prevented by use of externally generated electromotive force. Gold electrodes provide the most effective bactericidal effect. Silver, platinum, copper or stainless steel are less effective at currents which have no significant effect on surrounding tissue.

SUMMARY OF THE INVENTION

An apparatus having a surface with biological activity consequent to contact to the apparatus with an electrolyte includes an article and a plurality of different conducting materials. The materials are in contact with each other, and at least one of the materials is also in contact with a surface of the article whereby biological activity is imparted to the surface of the apparatus. The preferred biological activity is antimicrobial activity. The preferred conducting materials are metals, and preferred articles are medical devices such as catheters which connect an external environment with an internal body environment.

Metals which are particularly suitable in accordance with the invention are aluminum, silver, gold and platinum. Preferred metal combinations are silver-platinum, aluminum-silver, aluminum-gold and aluminum-platinum. Use of these preferred combinations imparts significantly greater antimicrobial activity to the surface of the apparatus of the invention than the sum of the antimicrobial effects observed on use of the metals independently.

In one embodiment of the apparatus, the metals are in contact with each other through a switch so that, if desired, the biological activity can be turned on or off.

In another aspect of the invention, there is provided a method to induce biological activity in an environment consequent to the use of the apparatus of the invention which includes bringing a surface of the apparatus into contact with an electrolyte in the environment. A preferred embodiment of this aspect of the invention is a method to inhibit growth of microorganisms consequent to catheterization which includes modifying a urinary or intravenous catheter with a plurality of metals, and treating a living body by contacting the modified catheter with a body electrolyte such as urine or blood.

The apparatus of the invention has synergistically improved antimicrobial surface activity in comparison to that of prior art surfaces which is provided by the use of a plurality of metals in certain combinations. The magnitude and duration of the antimicrobial activity may be controlled by varying the quantities of the metals used. It is believed that the use of two or more metals in contact with each other and with a body electrolyte sets up a galvanic action, and that the current thereby produced greatly enhances the oligodynamic antimicrobial effects over the prior art methods. It is further believed that the galvanic action provides the high metal ion concentrations achieved by iontophoresis induced by electrodes while avoiding the inconvenience of a cumbersome external power supply and the potential danger of tissue damage due to application of too much current.

In accordance with the preferred method for application of the metals to the device, the metallic surface of the apparatus is bright, lustrous and exceptionally smooth whereby problems associated with rough surfaces in contact with body tissues are substantially reduced. Problems particularly exacerbated by rough surfaces are the formation of thrombi during use of venous catheters and encrustation of materials causing serious patient discomfort during use of indwelling urinary catheters. In addition, apparatus having metals applied by the preferred method is inexpensive to manufacture because only small quantities of each metal are required to provide antimicrobial activity.

BRIEF DESCRIPTION OF THE DRAWINGS

FIG. 1 is a perspective view of a catheter section having two metals attached in accordance with the invention;

FIG. 2 is a cross-sectional view of the catheter section of FIG. 1 taken along line 2—2;

FIG. 3 is a cross-sectional view of a catheter section having two metal bands attached and connected through a switch;

DETAILED DESCRIPTION OF THE INVENTION

Figure 4:
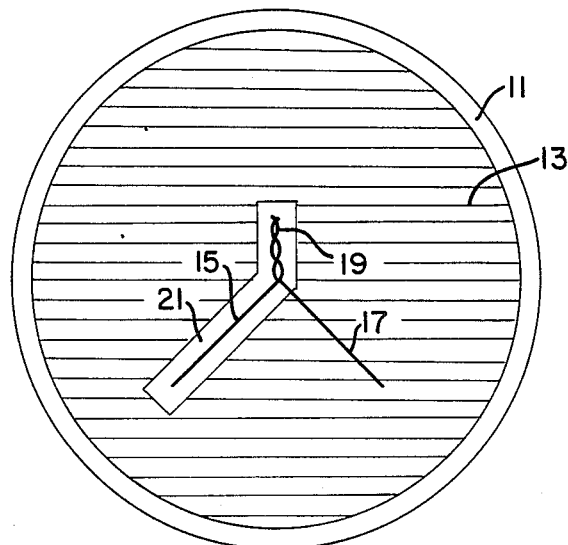
FIG. 4 is a plan view of a Petri dish having growth medium and microorganism growth illustrating a zone of growth inhibition by a combination of wires of two different metals.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

This invention is directed to an apparatus which induces biological activity during use in an environment and to a method to impart biological activity to a surface of the apparatus. The preferred biological activity is antimicrobial activity. Thus, for example, it is contemplated that the apparatus of the invention may be used for inhibition of microorganism growth in the processing or packaging of foods, or, preferably, in the practice of medicine. Other uses of the apparatuses of the invention are, for example, to promote bone healing by galvanic action, to deliver a drug by iontophoresis, to reduce thrombogenicity, to induce tissue or nerve regeneration, or most preferably, to treat a living body by connecting an external environment with an internal body environment.

Preferred apparatuses in accordance with the invention are modified medical devices such as, for example, modified catheters, tracheal tubes, insulin pumps, wound closures or drains, stopcocks, connectors, prosthetic devices, pacemaker leads, needles and the like. Most preferably, the apparatus of the invention remains in contact with the body for a period of time such that, without modification of the device surface in accordance with the invention, microorganism growth in association with use of the device would occur. The most preferred apparatus of the invention is a modified catheter, in particular an indwelling urinary catheter.

The device of the invention may be made of any suitable material, such as, for example, metal, glass, plastic, rubber, ceramic, or the like. Preferred materials are polyvinyl chloride, polyurethane, latex, or, most preferably, silicones or polyolefins, such as polyethylene, polypropylene and polytetrafluoroethylene. The device may be of any desired shape which in general will be determined by the intended use of the apparatus. For example, the shape of the device may be essentially flat, such as a sheet, or wafer, or it may have substantial thickness, as in a disc or a rod. Many devices contemplated by the present invention are hollow and thus may present both interior and exterior surfaces to invading microorganisms. Exemplary of such preferred hollow devices falling within the scope of the invention are connectors, adapters, hoses, tubes and the like.

In accordance with the invention, biological activity is imparted to the apparatus by affixing to the device a plurality of conducting materials. The term conducting materials is herein understood to mean a conductor or semiconductor, and includes metals and oxidized forms thereof. For example, the conducting materials may be a metal and a metal salt, such as, silver and silver chloride. Any combination of conducting materials which interact on a surface to impart biological activity to that surface fall within the scope of the invention, particularly those combinations which provide synergistic results.

In the embodiment of the invention wherein the device itself is made of conducting material, only a single conducting material need be affixed to the device to provide biological surface activity in accordance with the invention: Exemplary of this embodiment of the invention is an aluminum or steel needle having silver thereon.

It has been found that when suitable combinations or conducting materials are affixed to the device surface, migration of microorganisms along the surface of the apparatus is inhibited. Further, growth of microorganisms in the internal body environment proximate to the surface of the apparatus is also inhibited.

Preferred conducting materials are metals wherein at least one of the metals is in contact with a surface of the device, and each metal is in contact with at least one other metal. The term contact is herein understood to include both physical contact and contact through any appropriate electrical conducting path. Preferred metal combinations are aluminum and a noble metal such as silver, gold or platinum. The most preferred combination is silver and platinum.

A mixture of the metals in particulate form may be coated on all or part of the surface of the device, or the mixture may be added to a monomer before polymerization or to a polymer before fabrication so that the mixture is incorporated into the body of the device. Alternatively, the metals may be coated, one over the other, onto all or part of the surface of the device or they may be applied in the form of bands or wires. Pure metals may be used, or the metals may be used in the form of alloys which contain one or more other materials. The preferred method of application is to sputter a film of the metals onto the surface of the article. The metals may be premixed by any suitable method, and the mixture sputtered onto the device, or most preferably, films of the metals may be sputtered onto the device sequentially so that the film of one metal is layered over the film of the other. This preferred method is most economical as smaller quantities of metal are required and the surface thereby obtained is bright, lustrous and exceptionally smooth. The films applied by sputtering may be from about 5 to 500 nm, preferably 20 to 200 nm thick. If desired, the entire apparatus or any portion thereof, may be covered with a material, such as a hydrogel or a lubricant, which is permeable to ions.

Turning now to the Figures, there is shown in FIG. 1 a perspective view of an apparatus 10 consisting of catheter section 12 having wall portion 14 and bore 16. Wall portion 14 has metal film 18 affixed thereto, and film 20 of a different metal sputtered over metal film 18.

FIG. 2 is a cross-sectional view of the catheter section of FIG. 1 showing metal films 18 and 20 affixed to catheter wall portion 14 as described for FIG. 1.

FIG. 3 is a cross-sectional view of an embodiment of the invention in which catheter section 12a has metal films 18a and 20a thereon separated by a space 22 whereby the two films are not in contact when switch 24 is open but which are in contact when switch 24 is closed. Thus, when switch 24 is closed, a galvanic cell is established and biological activity is initiated. Preferably, switch 24 is connected by lead 26 to the external environment whereby the biological activity may be turned on or off.

In another aspect of the invention, a method to inhibit growth of microorganisms in an environment is provided by contacting the apparatus with an electrolyte in the environment. In a preferred embodiment of the method, the apparatus includes a medical device and is used to treat a living body. The apparatus is brought into contact with an electrolyte of the body to provide antimicrobial activity by galvanic release of mobile metal ions into the surrounding body environment. The electrolyte may be a body tissue or preferably a body fluid, such as, for example, blood, urine or the like.

The invention is best described by an in vitro system which clearly demonstrates the synergistic effect obtained by use of two metals in contact. FIGS. 4–9 illustrate ordinary petri dishes containing conventional bacterial growth media, such as trypticase soy agar (TSA), which have been inoculated with various microorganisms such that growth spreads essentially uniformly over the entire plate. Embedded in the surfaces of the media are wires of various metals or metal combinations, or sections of conventional catheters which have been coated with various metals or metal combinations.

FIG. 4 shows petri dish 11 containing TSA which is evenly covered with growth 13 of *Staphylococcus aureus* (SA). Silver wire 15 and platinum wire 17 are embedded in the surface of the TSA and are in contact at twisted area 19. Growth 13 covers the entire surface of the TSA except for zone 21 proximate to silver wire 15 and twist 19 where growth is inhibited. No inhibition occurs proximate to platinum wire 17. The same result is obtained when the experiment is repeated with aluminum in contact with silver, platinum, or gold, in which experiments the zones of growth inhibition are around the wire of the noble metal. Zones of inhibition corresponding to zone 21 are also observed using each metal combination with the bacteria *Staphylococcus saprophyticus* (SS), *Staphylococcus epidermidis* (SE), *Streptococcus facecalis* (SF), *Escherichia coli* (EC), *Pseudomonas aeruginosa* (PA), *Klebsiella pneumoniae* (KP), and the yeast *Candida albicans* (CA).

Figure 5:
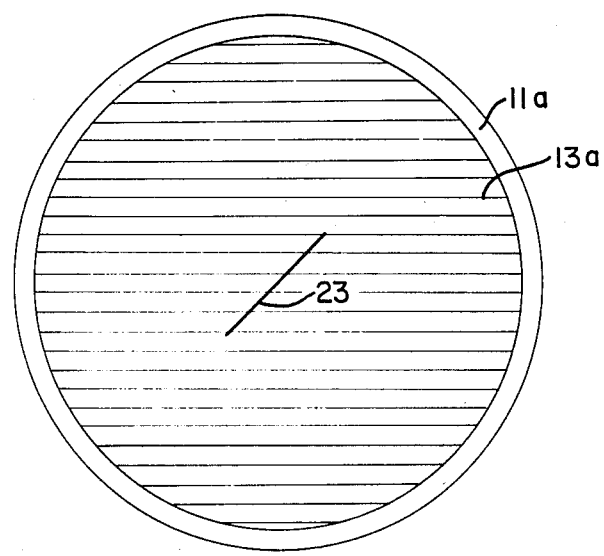
FIG. 5 is a plan view of a Petri dish having growth medium and microorganism growth illustrating no zone of growth inhibition by a single metal wire.

When a single metal wire is used, no significant inhibition of growth of any of the above microorganisms occurs. FIG. 5 shows wire 23 of silver, gold, platinum or aluminum embedded in the surface of TSA. Growth 13a extends all the way to the metal and no zone of inhibition develops when wire 23 is platinum, gold or aluminum. When wire 23 is silver, a narrow zone of partial inhibition of EC growth is sometimes observed (but is not illustrated in FIG. 5). Silver wire 23 has no effect against the other test organisms listed above.

Figure 6:
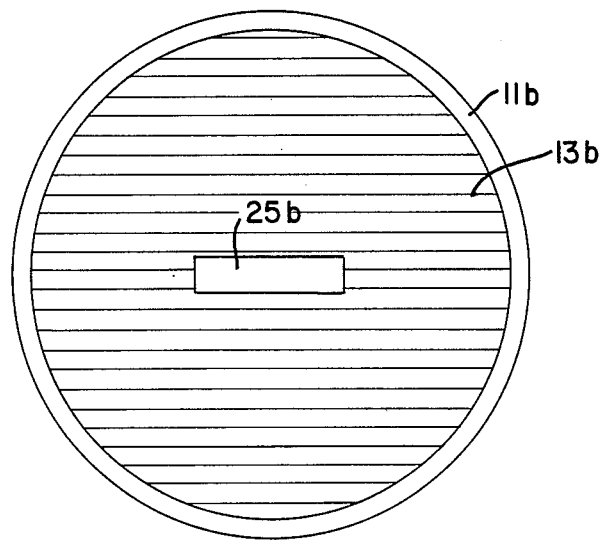
FIG. 6 is a plan view of a Petri dish having growth medium and microorganism growth illustrating no zone of growth inhibition around a catheter section devoid of wire.
Figure 7:
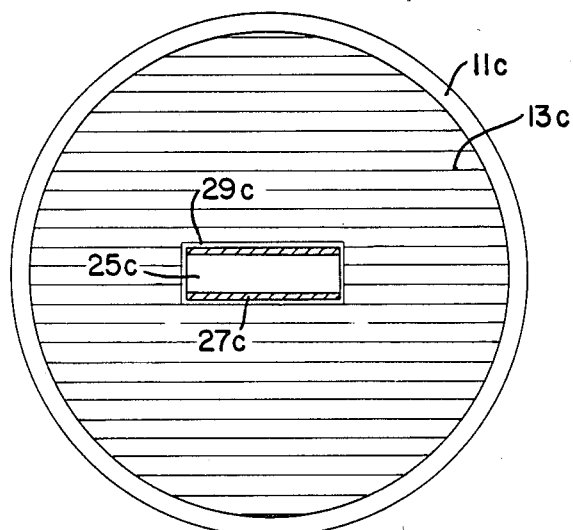
FIG. 7 is a plan view of a Petri dish having growth medium and microorganism growth illustrating a narrow and insignificant zone of growth inhibition around a catheter section having a coating of silver.
Figure 8:
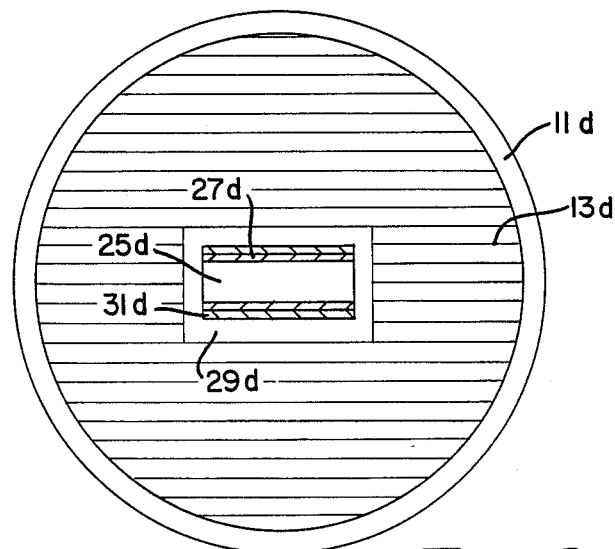
FIGS. 8 and 9 are plan views of Petri dishes having growth medium and microorganism growth illustrating extensive zones of growth inhibition around catheter sections having coatings of silver and platinum.

FIGS. 6–8 show petri dishes 11b, 11c and 11d containing hollow silicone urinary or intravenous catheter sections embedded in TSA after inoculation with SA or EC and incubation for 18 hours at 37 degrees Celsius. Catheter section 25b in FIG. 6 is a negative control with no metal on its surface. Microorganism growth occurs uniformly up to the catheter section and no inhibition is seen. In FIG. 7, a 20 nm film of silver 27c is sputtered onto catheter section 25c. A narrow band of incomplete growth inhibition 29c is seen to surround the catheter section. In FIG. 8, a 20 nm film of platinum 27d is sputtered onto catheter section 25d, and is covered with a 20 nm film of sputtered silver 31d. A broad zone 29d having no bacterial growth is seen to surround catheter section 25d. A similar result may be observed if the films of platinum and silver are reversed so that silver is on the catheter section.

Figure 9:
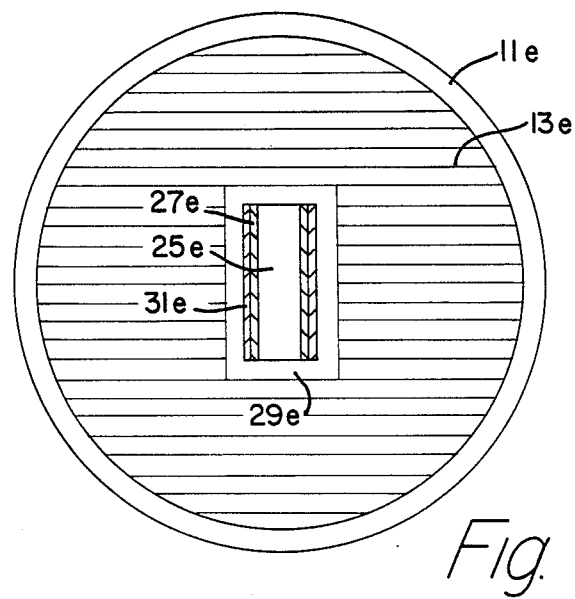

Inhibition of the growth of SA or EC by the silver-platinum combination on a section of silicone urinary catheter of the Foley type is illustrated in FIG. 9. Silver film 27e on catheter section 25e is covered with platinum film 31e. Complete inhibition of growth in zone 29e is seen. A similar result is observed if the metal films are reversed. In contrast, no zone of inhibition occurs around a section of silicone Foley catheter without contact with the metal combination.

It is believed, although as yet unsubstantiated, that the metals used in accordance with the method of the invention provide high antimicrobial activity by one or more of several mechanisms. They may interact to form hydrogen peroxide from components of the environment surrounding the apparatus. It is believed that hydrogen peroxide generation is the mechanism which predominates in the experiments involving aluminum. In a second mechanism, the metals may interact to release metal ions into surrounding environment. It is believed that metal ion release is the mechanism which predominates in experiments using only noble metals. It is further believed that a significantly higher concentration of metal ions is released into the surrounding environment than occurs if the metals act independently, and that the high ion concentration results from formation of a galvanic cell by the metals when they are in contact with each other and with an electrolyte.

Figure 10:
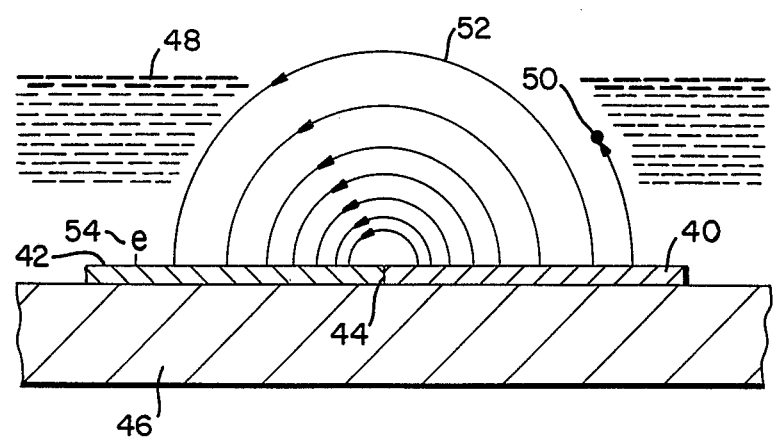
FIG. 10 is a cross-sectional view of a catheter section having two metals attached schematically illustrating galvanic action and an ion flux through an electrolyte.

It is well-known that metals in contact may form a galvanic cell when immersed in an electrolyte. FIG. 10 illustrates formation of metal ions by the galvanic action of the apparatus of the present invention. Metals 40 and 42 are in contact at point 44 on catheter surface 46. The apparatus is immersed in electrolyte 48. Galvanic action between metals 40 and 42 causes oxidation of metal 40 to ion 50 which diffuses into the surrounding medium as ion flux 52. Electron 54 passes through contact point 44 from metal 40 to metal 42 where it reduces a component of the electrolyte.

In the case of the in vitro system used to describe the invention, the electrolyte is in the growth medium. When apparatus of the invention is used in a living body, the electolyte may be present in a body tissue or fluid such as blood, urine and the like. Generation of hydrogen peroxide or substantially greater concentrations of metal ions by galvanic action induced by the use of two or more metals in contact with a medical device represents a significant and wholly unexpected improvement over known methods to inhibit growth of microorganisms and resultant infection consequent to use of the device.

EXAMPLE I

Wires (8 mil gauge) of silver, platinum, gold and aluminum 1.5 inches long were bent to an angle of 45 degrees so that the two sections were 1 inch and 0.5 inch in length. The short ends of wires of different metals were twisted together to provide Y-shaped combinations of the metals (similar to the wires illustrated in FIG. 4). The wire combinations were embedded in the surface of solidifying TSA which had previously been inoculated with pure cultures of SA, SS, SE, EC, PA and CA prior to pouring of the plate and incubated for 18 hours at 37 degrees Celsius. Zones of growth inhibition from about 5 to 6 mm wide developed around the silver wire twisted with platinum and around gold, silver, or platinum wires twisted with aluminum. No clear zone of inhibition were evident with silver-gold and gold-platinum combinations.

EXAMPLE II

The experiment of Example I was repeated using single straight wires of aluminum, silver, gold and platinum. Zones of growth inhibition were very small or did not develop at all. Likewise, no significant inhibition of growth occurred when wire combinations which give inhibition when in contact were embedded adjacent each other but not touching.

EXAMPLE III

The experiment of Example I was repeated using 1 inch sections of silicone urinary and intravenous catheters. A 20 nm film of platinum was sputtered onto the catheter section and a 20 nm film of silver was sputtered thereon. Zones of inhibition up to 10.5 mm wide formed around the catheter sections in a manner similar to that described for Example I. Control experiments with catheter sections containing no metal or a single metal gave no significant inhibition of growth.

Thus, in accordance with the invention, an apparatus includes a plurality of metals on a medical device wherein at least one of the metals is in contact with a surface of the device, and each metal is in contact with at least one other metal. When the apparatus contacts an electrolyte, as, for example, a body electrolyte contacted when the apparatus is used to treat a living body, the apparatus surface exhibits antimicrobial activity which inhibits growth of microorganisms in the body consequent to use of the apparatus. It has surprisingly been found that the plurality of metals imparts antimicrobial activity which is far in excess of that obtained when the metals are not in contact wherein they act independently giving merely additive antimicrobial activity. This wholly unexpected synergistic effect is believed to be due to formation of hydrogen peroxide or formation of metal ions by galvanic action.

What is claimed is:

1. An apparatus comprising a medical device, a switch and a plurality of metals, a first of said metals being a coating on a surface of said device and a second of said metals being in contact with a surface of said device, said first and second metals defining a space therebetween, said switch being affixed to one of said metals, said metals being connected to each other through said switch when said switch is closed but unconnected when said switch is open, whereby biological activity is imparted to a surface of the apparatus consequent to contact of said apparatus with an electrolyte of a living body when said switch is closed.

* * * * *